(12) United States Patent
O'Lenick et al.

(10) Patent No.: US 8,273,796 B2
(45) Date of Patent: Sep. 25, 2012

(54) POLY CATIONIC COMPOUNDS

(75) Inventors: Kevin A. O'Lenick, Dacula, GA (US); Anthony J. O'Lenick, Jr., Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 318 days.

(21) Appl. No.: 12/802,039

(22) Filed: Jun. 1, 2010

(65) Prior Publication Data

US 2010/0239516 A1  Sep. 23, 2010

Related U.S. Application Data

(63) Continuation-in-part of application No. 12/080,073, filed on Apr. 1, 2008, now Pat. No. 7,750,044.

(51) Int. Cl.
*A61K 31/14* (2006.01)
*A61K 31/195* (2006.01)
*C07C 69/74* (2006.01)
*C07C 233/05* (2006.01)

(52) U.S. Cl. ........ 514/642; 514/563; 514/529; 514/547; 514/558; 560/127; 560/182; 554/37; 554/35; 554/52; 554/63

(58) Field of Classification Search .................. None
See application file for complete search history.

(56) References Cited

U.S. PATENT DOCUMENTS

| | | | |
|---|---|---|---|
| 6,861,542 B1 * | 3/2005 | O'Lenick et al. | 554/35 |
| 6,979,744 B1 * | 12/2005 | O'Lenick et al. | 554/63 |
| 7,148,256 B1 * | 12/2006 | O'Lenick et al. | 514/558 |
| 7,193,111 B1 * | 3/2007 | O'Lenick et al. | 564/153 |
| 7,750,044 B2 * | 7/2010 | O'Lenick et al. | 514/529 |

* cited by examiner

*Primary Examiner* — Yate K Cutliff

(57) ABSTRACT

The present invention relates to a novel class of polymeric compounds having specific quaternized amine based upon a dimer acid reacted with a combination of a monohydroxy functional amine and a specific di-hydroxy functional tertiary alkanolamine, to make an ester tertiary amine, which is a subsequent step is converted to a quaternary compound. Dimer acid is a C-36 diacid having a cyclic structure and reacting it with the two type of amine groups allow for the synthesis of a high molecular weight cationic compound which is extremely substantitive to human skin and are well tolerated by human tissue making them suitable for use preparation of barrier products for personal care applications. These materials are dimethylaminopropyl amine free, which is highly desirable in personal care applications.

19 Claims, No Drawings

POLY CATIONIC COMPOUNDS

RELATED APPLICATION

This application is a continuation in part of U.S. Ser. No. 12/080,073, filed Apr. 1, 2008 now U.S. Pat. No. 7,750,044

FEDERAL SPONSORSHIP

None

FIELD OF THE INVENTION

The present invention relates to a novel class of polymeric compounds having specific quaternized amine based upon a dimer acid reacted with a combination of a monohydroxy functional amine and a specific di-hydroxy functional tertiary alkanolamine, to make an ester tertiary amine, which is a subsequent step is converted to a quaternary compound. Dimer acid is a C-36 diacid having a cyclic structure and reacting it with the two type of amine groups allow for the synthesis of a high molecular weight cationic compound which is extremely substantitive to human skin and are well tolerated by human tissue making them suitable for use preparation of barrier products for personal care applications. These materials are dimethylaminopropyl amine free, which is highly desirable in personal care applications.

BACKGROUND OF THE INVENTION

It is very desirable to provide a material from aqueous solution that will condition the hair and still be compatible with anionic surfactants. This allows for the preparation of clear two in one shampoo systems, clear 2 in one shower gels, and clear two in one bath products. By two in one products in meant, a product that contains both anionic surfactant, most commonly sulfates and ether sulfates and a cationic conditioning agent. The anionic surfactant is the detergent, which cleans the hair or skin, and the cationic product is for conditioning providing softness, slip and feels to the skin. The problem with such product has always been the incompatibility of the anionic and cationic surfactants with each other. When many of these products are present in the same solution an insoluble salt forms making a cosmetically unacceptable white gunk that does not stay in solution.

As will become clear, by making a very large molecule the present invention results in a soft quaternary compound. By soft quaternary compound is meant one that not withstanding its cationic charge is of a structure so that when placed in water along with the anionic surfactant, a clear stable solution is obtained. Surprisingly, because of the high molecular weight of the quaternary compound, the deposition on the hair and skin is increased. While not wanting to be held to only one mechanism, we believe there rather than a precipitate observed with so-called hard quats, compounds of the present invention form a self-assembling complex between the anionic and cationic surfactant. This complex, while water-soluble is large enough to disrupt hydrogen bonding between water molecules, and as such energetically, the complex will be deposited on the skin or hair leaving the remaining solution at the lowers free energy level.

The self-assembling aspect of the present invention, which we believe is the result of orientation of the salt of the cationic compounds of the present invention and the anionic surfactants present in solution, can be demonstrated by the fact that upon initial mixing of the components, a hazy or cloudy dispersion occurs. With suitable mixing, this hazy dispersion becomes a solution and the viscosity increases.

The compounds of the present invention can be formulated into body washes and other skin products and hair care products to provide a "delivery system" for conditioning the hair or skin. The high molecular weight of the quat and the fact that the point charges are far apart in the molecule results in through and efficient deposition on the hair or skin. This provides uniformity of conditioning agent over the entire hair of skin surface. This is particularly important for applications on hair for people with long hair. In general the long hair is more damaged, dry and in need of conditioning at the tip area, than near the root. The hair closest to the scalp is newer, less damaged, and less in need of conditioning. This dichotomy of hair condition is more effectively treated by the complexes formed by the current invention than by other quats. In addition, the di-nature of the compounds provides for outstanding substantivity of the molecule allow for very mild natural like materials that can be used in products where low irritation is important.

U.S. Pat. No. 5,811,385 describes a process for making high active aqueous solutions of ester quats. It states "The invention relates to high-concentration aqueous solutions of quaternary carboxylic acid alkanolamine ester salts, a process for preparing these solutions and their use. Quaternary carboxylic acid alkanolamine ester salts, also named ester quats, are highly active cationic surfactants with many uses. Thus, these surfactants are suitable, for example, as fabric softeners, cosmetic bases, active compounds with respect to soil release and soil redeposition, antistatic agents, fabric finishes, biocide and phase-transfer catalysts. Since these ester quats, owing to their biodegradability, are also ecologically advantageous, they have recently substantially replaced the classic fatty alkyl quats such as distearyl-dimethylammonium chloride."

The ester quats of the U.S. Pat. No. 5,811,385 invention are not polymeric and as such are not delivery systems as are the products of the present invention. It is only by selecting the particular novel dimer acid alkanolamine ester that the polymeric quats of the present invention can be made.

SUMMARY OF THE INVENTION

Objective of the Invention

It is the objective of the invention to provide a novel series of polymeric dimer alkanolamine ester quaternary compounds and a process of its use which comprises contacting the skin with an effective conditioning concentration of the novel quaternary compounds when applied in aqueous solution containing anionic surfactants. These anionic surfactants are preferably fatty sulfates and fatty ether sulfates having between 1 and 4 moles of ethylene oxide present. The polymeric nature of these materials makes them very substantive and minimally penetrating to the skin, making them both non-toxic and non-irritating.

In accordance with the present invention, we have now been discovered novel quaternary compound, which conforms to the following structure:

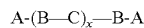

wherein:

A is —O—CH$_2$CH$_2$—N$^+$(CH$_3$)$_3$Cl$^-$

B is derived from the group consisting of:

(i) dimer acid conforming to the following structure:

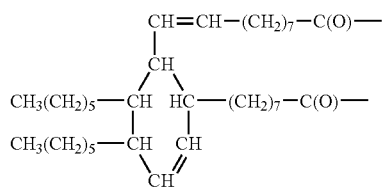

(ii) hydrogenated dimer acid conforming to the following structure:

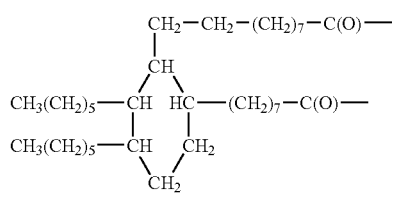

or (iii) mixtures thereof;

C is derived from methyl diethanolamine and conforms to the following structure:

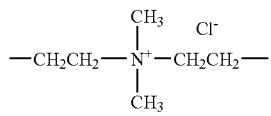

x is an integer ranging from 1 to 2,000.

The difference between the two dimer species is that one of them has no double bond in the cyclic structure, while the first has a double bond. The double bond is removed by hydrogenation of the acid prior to making the quaternary compound. This variation has lighter color and better oxidative stability, making it prized for cosmetic applications where a water white product is desired. Consumers consider water white products as cleaner and more appealing over yellow products.

The present invention is also directed to a process for very efficiently conditioning the skin and hair from aqueous solution containing anionic surfactant. The complex that forms is very efficient in providing conditioning and can be used at concentrations as low as 0.5% by weight in a shampoo formulation. This is very important in products where low irritation is important like baby shampoo and bubble bath products.

Another aspect of the present invention is a process for conditioning hair comprises contacting the hair with an effective conditioning concentration of a quaternary compound, which conforms to the following structure:

A-(B—C)$_x$—B-A wherein:

A is —O—CH$_2$CH$_2$—N$^+$(CH$_3$)$_3$Cl$^-$

B is derived from the group consisting of:

(i) dimer acid conforming to the following structure:

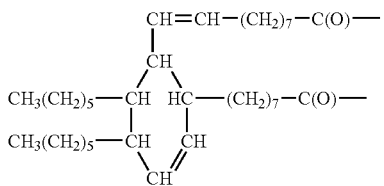

(ii) hydrogenated dimer acid conforming to the following structure:

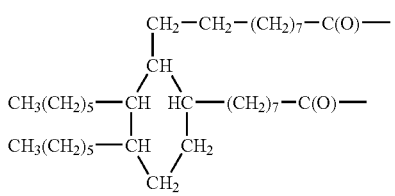

or (iii) mixtures thereof;

C is derived from methyl diethanolamine and conforms to the following structure:

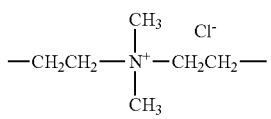

x is an integer ranging from 1 to 2,000.

The preferred effective conditioning concentration ranges from 0.5% to 25% by weight.

An additional aspect of the present invention is two intermediates that are made by the reaction of methyl diethanolamine, dimethyl ethanolamine and dimer acid. They conform to the following structure:

D-(E—F)$_x$—B-D wherein:

D is —O—CH$_2$CH$_2$—N(CH$_3$)$_2$

E is derived from the group consisting of:

(i) dimer acid conforming to the following structure:

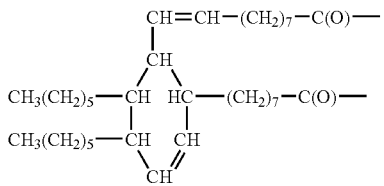

(ii) hydrogenated dimer acid conforming to the following structure:

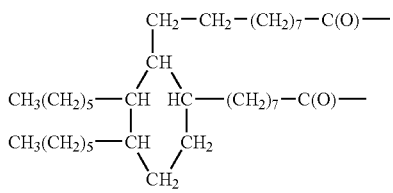

or (iii) mixtures thereof;

F is derived from methyl diethanolamine and conforms to the following structure:

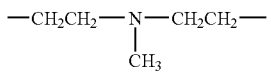

x is an integer ranging from 1 to 2,000.

These strategic intermediates are necessary to make the compounds of the present invention. The selection of tertiary amines that have one hydroxyl group (dimethyl ethanolamine) and a tertiary amine with two hydroxyl groups, methyl diethanolamine is critical to the reaction. Mono hydroxyl tertiary amines cannot form amides, and by virtue of their mono functionality act as chain stoppers, while di hydroxyl tertiary amines cannot form amides, and by virtue of their di functionality act as chain extenders when reacted with dimer acid.

The polymers of the present invention are made in polar solvent, typically water, but can also be made in propylene glycol, polyoxyalkylene glycols and PEG/PPG dimethicone or combinations thereof. The selection of the proper solvent or combinations of solvents will determine the viscosity of the final polymer.

The use of PEG/PPG dimethicone as a solvent results not only in a relatively low viscosity product, but also results in a composition that has extremely efficient deposition on hair and skin, making the compositions highly desirable in personal care applications.

Preferred Embodiments

In a preferred embodiment B is derived from dimer acid conforming to the following structure:

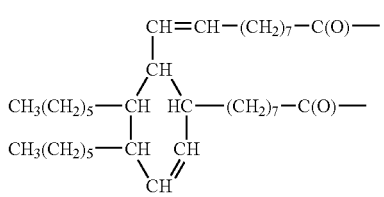

In another preferred embodiment B is derived from hydrogenated dimer acid conforming to the following structure:

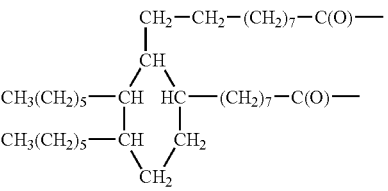

In still another preferred embodiment B is derived from a mixture of dimer acid and hydrogenated dimer acid.

In a preferred embodiment x is 1.
In a preferred embodiment x is 20.
In a preferred embodiment x is 100.
In a preferred embodiment x is 500.
In a preferred embodiment x is 1,000.
In a preferred embodiment x is 2,000.

DETAILED DESCRIPTION OF THE INVENTION

The present invention is directed to specific quaternary compound, which conforms to the following structure:

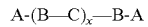

wherein:

A is —O—$CH_2CH_2$—$N^+(CH_3)_3Cl^-$
B is derived from the group consisting of:
(i) dimer acid conforming to the following structure:

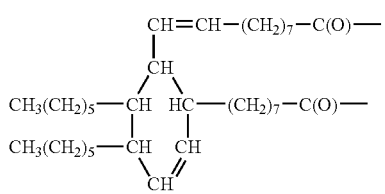

(ii) hydrogenated dimer acid conforming to the following structure:

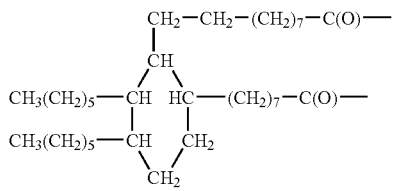

or (iii) mixtures thereof;

C is derived from methyl diethanolamine and conforms to the following structure:

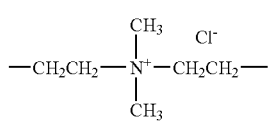

x is an integer ranging from 1 to 2,000.

The compounds of the present invention are made reaction of

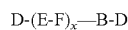

wherein:
D is —O—CH$_2$CH$_2$—N(CH$_3$)$_2$
E is derived from the group consisting of:
 (i) dimer acid conforming to the following structure:

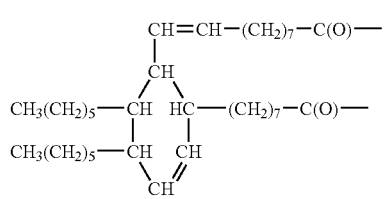

(ii) hydrogenated dimer acid conforming to the following structure:

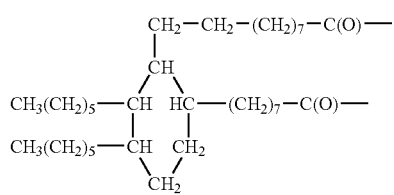

or
 (iii) mixtures thereof;
F is derived from methyl diethanolamine and conforms to the following structure:

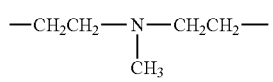

x is an integer ranging from 1 to 2,000,
with a quaternizing agent selected from the group consisting of methyl chloride, benzyl chloride, chloroglycerine and mixtures thereof.

Another aspect of the present invention is also directed to a process for very efficiently conditioning the skin and hair from aqueous solution containing anionic surfactant. The complex that forms is very efficient in providing conditioning and can be used at concentrations as low as 0.5% by weight in a shampoo formulation. This is very important in products where low irritation is important like baby shampoo and bubble bath products.

The process for conditioning hair comprises contacting the hair with an effective conditioning concentration of a quaternary compound, which conforms to the following structure:

A-(B—C)$_x$—B-A wherein:
A is —O—CH$_2$CH$_2$—N$^+$(CH$_3$)$_3$Cl$^-$
B is derived from the group consisting of:
 (i) dimer acid conforming to the following structure:

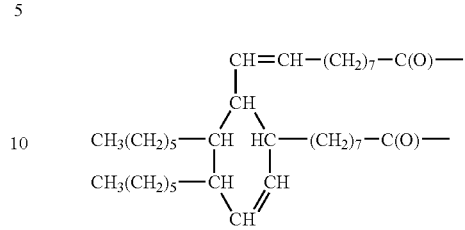

(ii) hydrogenated dimer acid conforming to the following structure:

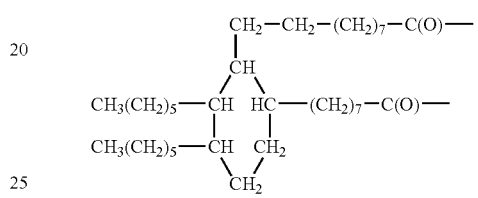

or
 (iii) mixtures thereof;
C is derived from methyl diethanolamine and conforms to the following structure:

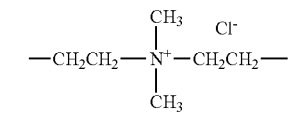

x is an integer ranging from 1 to 2,000.
The preferred effective conditioning concentration ranges from 0.5% to 25% by weight.

EXAMPLES

Monofunctional Tertiary Amine

Example 1

Dimethyl Ethanolamine (Also Called DMEA)

DMEA is an item of commerce commercially available from a variety of sources including Huntsman. It conforms to the following structure:

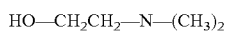
HO—CH$_2$CH$_2$—N—(CH$_3$)$_2$

It has a CAS number 108-01-0.
Di-functional Tertiary Amine (Methyl diethanolamine)

Example 2

Methyl Diethanolamine (Also Called MDEA)

MDEA is an item of commerce commercially available from a variety of sources including Huntsman. It conforms to the following structure:

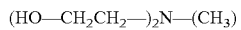
(HO—CH$_2$CH$_2$—)$_2$N—(CH$_3$)

It has a CAS number 105-59-9.

Example 3

Dimer Acid

Dimer acid is an item of commerce and is available from a variety of sources including Cognis Chemical Cincinnati Ohio. It conforms to the following structure:

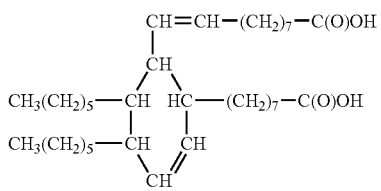

Example 4

Hydrogenated Dimer

Hydrogenated dimer acid is an item of commerce and is available from a variety of sources including Cognis Chemical Cincinnati Ohio. It conforms to the following structure:

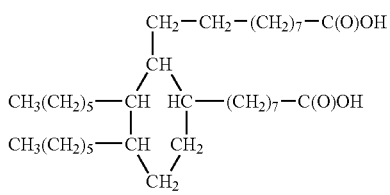

Example 5

Methyl Chloride

Methyl chloride is an item of commerce and is available from a variety of sources.
It conforms to the following structure:

It has a CAS number of 200-817-4.
Intermediate Polymers

The tertiary amine polymers (Examples 6-16) are prepared according to the following procedure:

To the specified number of grams of Example 1 is added the specified number of grams of 2, and the specified number of grams of 3 or 4 or both. The mixture is heated to 150 to 180 C., keeping the temperature of the distillate coming off at no more than 120 C. This temperature assures that minimal amounts of the amine distill off with the water made during the reaction. Once the temperature reaches 180 C. hold for 38 hours. An excess of the amine is added to speed up the reaction. When the acid value reaches 1.0 mg KOH/gram, the excess amine is stripped off by applying vacuum. The resulting product is the ester amine useful as an intermediate in the preparation of the compounds of the present invention.

| Example | Example 1 Grams | Example 2 Grams | Example | Grams | "x" value |
|---|---|---|---|---|---|
| 6 | 309 | 238 | 4 | 300 | 1 |
| 7 | 360 | 357 | 3 | 750 | 5 |
| 8 | 227 | 250 | 3 | 300 | 20 |
|   |     |     | 4 | 300 |    |
| 9 | 105 | 120 | 3 | 300 | 100 |
| 10 | 515 | 596 | 3 | 1000 | 500 |
|    |     |     | 4 | 500 |     |
| 11 | 103 | 119 | 3 | 300 | 1000 |
| 12 | 148 | 171 | 3 | 451 | 1500 |
| 13 | 195 | 240 | 4 | 610 | 2000 |

The compounds are used without additional purification.
Preparation of the Cationic of the Present Invention The compounds In a stainless Parr autoclave was added the specified number of grams of the specified intermediate (example 6-13). Next add 10.7 grams of sodium bicarbonate, and 200 grams of butylene glycol. The autoclave is sealed, agitation applied and a nitrogen purge applied. The temperature is raised to 85 C. Next add the specified number of grams of methyl chloride slowly, so that the temperature is maintained between 80 C. and 90 C. After all the methyl chloride is added, keep the temperature at 80 C. for two hours under agitation. Cool down and filter. The product is used without are yellow liquids as prepared.

|  | Intermediate |  | Methyl Chloride |
|---|---|---|---|
| Example | Example | Grams | Grams |
| 14 | 6 | 847 | 60 |
| 15 | 7 | 1467 | 300 |
| 16 | 8 | 1077 | 12 |
| 17 | 9 | 525 | 60 |
| 18 | 10 | 2611 | 300 |
| 19 | 11 | 522 | 60 |
| 20 | 12 | 782 | 90 |
| 21 | 13 | 1044 | 120 |

The compatibility of this novel quaternary ester compounds of the invention with human tissue, i.e., dermal and eye tissue has been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

We claim:
1. A quaternary compound, which conforms to the following structure:

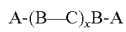

wherein:

A is —O—CH$_2$CH$_2$—N$^+$(CH$_3$)$_3$Cl$^-$

B is derived from the group consisting of:
(i) dimer acid conforming to the following structure:

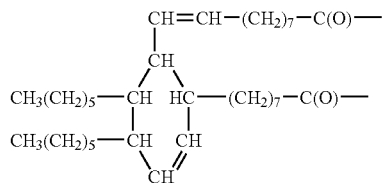

(ii) hydrogenated dimer acid conforming to the following structure:

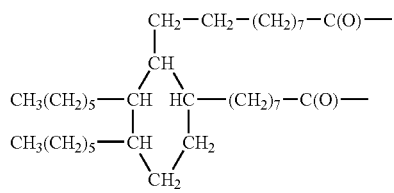

or
(iii) mixtures thereof;

C is derived from methyl diethanolamine and conforms to the following structure:

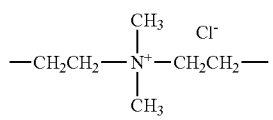

x is an integer ranging from 1 to 2,000.

2. A quaternary compound of claim 1 wherein B conforms to the following structure:

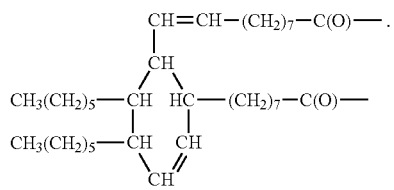

3. A quaternary compound of claim 1 wherein B conforms to the following structure:

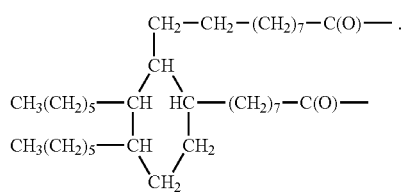

4. A quaternary compound of claim 1 wherein B is a mixture of

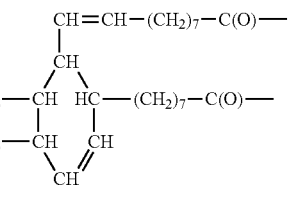

and

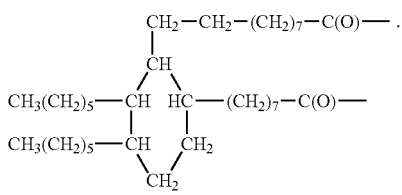

5. A quaternary compound of claim 1 wherein x is 1.

6. A quaternary compound of claim 1 wherein x is 20.

7. A quaternary compound of claim 1 wherein x is 100.

8. A quaternary compound of claim 1 wherein x is 500.

9. A quaternary compound of claim 1 wherein x is 1,000.

10. A quaternary compound of claim 1 wherein x is 2,000.

11. A process for conditioning hair which comprises contacting the hair with an effective conditioning concentration of a quaternary compound, which conforms to the following structure:

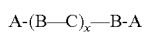

wherein:

A is —O—CH$_2$CH$_2$—N$^+$(CH$_3$)$_3$Cl$^-$

B is derived from the group consisting of:
(i) dimer acid conforming to the following structure:

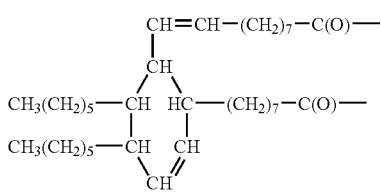

(ii) hydrogenated dimer acid conforming to the following structure:

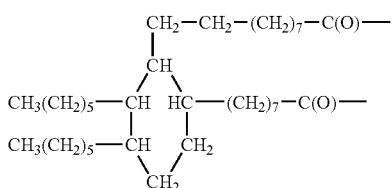

or
(iii) mixtures thereof;

C is derived from methyl diethanolamine and conforms to the following structure:

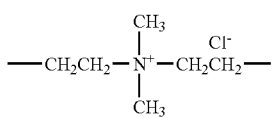

x is an integer ranging from 1 to 2,000.

12. A process of claim 11 wherein said effective conditioning concentration ranges from 0.5% to 25% by weight.

13. A process of claim 11 wherein B conforms to the following structure:

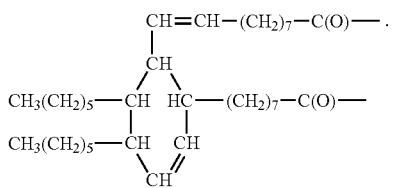

14. A process of claim 11 wherein B conforms to the following structure:

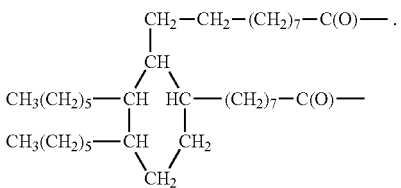

15. A process of claim 11 wherein x is 1.
16. A process of claim 11 wherein x is 20.
17. A process of claim 11 wherein x is 100.
18. A process of claim 11 wherein x is 500.
19. A process of claim 11 wherein x is 1,000.

* * * * *